United States Patent
Arai et al.

(10) Patent No.: US 6,723,070 B1
(45) Date of Patent: *Apr. 20, 2004

(54) BALLOON CATHETER

(75) Inventors: Takashi Arai, Kasugai (JP); Nobumasa Tsutsui, Nagoya (JP)

(73) Assignee: K. K. Vayu, Nagoya (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/322,950

(22) Filed: May 28, 1999

(30) Foreign Application Priority Data

Jun. 2, 1998 (JP) .......................................... 10-152887

(51) Int. Cl.⁷ .............................................. A61M 29/00
(52) U.S. Cl. .................................. 604/96.01; 604/93.01
(58) Field of Search ................................ 604/174, 178, 604/264, 96, 96.01, 93.01, 180, 280, 282, 103.12, 164.12; 606/194, 108, 192, 198

(56) References Cited

U.S. PATENT DOCUMENTS

| | | | | |
|---|---|---|---|---|
| 4,285,341 A | * | 8/1981 | Pollack .................... 128/214 R |
| 4,503,569 A | * | 3/1985 | Dotter ............................. 3/1.4 |
| 4,878,906 A | * | 11/1989 | Lindemann et al. ............ 623/1 |
| 4,994,032 A | * | 2/1991 | Sugiyama et al. ............. 604/96 |
| 5,439,447 A | | 8/1995 | Miraki ......................... 604/96 |
| 5,466,222 A | * | 11/1995 | Ressemann et al. .......... 604/96 |
| 5,569,219 A | * | 10/1996 | Hakki et al. ................ 604/282 |
| 5,571,089 A | * | 11/1996 | Crocker ....................... 604/102 |
| 5,634,902 A | | 6/1997 | Johnson et al. ............... 604/96 |
| 5,637,086 A | | 6/1997 | Ferguson et al. .............. 604/53 |
| 5,667,521 A | * | 9/1997 | Keown ......................... 606/194 |
| 5,782,811 A | * | 7/1998 | Samson et al. .............. 604/282 |
| 5,836,925 A | * | 11/1998 | Soltesz ......................... 604/280 |
| 5,855,563 A | * | 1/1999 | Kaplan et al. ................. 604/49 |
| 5,968,068 A | * | 10/1999 | Dehdashtian et al. ........ 606/192 |
| 5,989,218 A | * | 11/1999 | Wasicek ....................... 604/96 |
| 6,021,340 A | * | 2/2000 | Randolph et al. ............ 600/381 |
| 6,117,106 A | * | 9/2000 | Wasicek et al. ........... 604/96.01 |
| 6,254,611 B1 | * | 7/2001 | Vrba ........................... 606/108 |
| 6,319,244 B2 | * | 11/2001 | Suresh et al. ................ 604/525 |
| 6,319,275 B1 | * | 11/2001 | Lashinski et al. ........... 623/1.11 |
| 6,322,577 B1 | * | 11/2001 | McInnes ...................... 606/194 |
| 6,371,961 B1 | * | 4/2002 | Osborne et al. ............. 606/108 |
| 6,425,898 B1 | * | 7/2002 | Wilson et al. ............... 606/108 |
| 6,482,171 B1 | * | 11/2002 | Corvi et al. .............. 604/96.01 |
| 6,506,180 B1 | * | 1/2003 | Lary ....................... 604/103.12 |
| 6,544,230 B1 | * | 4/2003 | Flaherty et al. ......... 604/164.12 |
| 6,544,276 B1 | * | 4/2003 | Azizi ........................... 606/159 |

FOREIGN PATENT DOCUMENTS

EP  0 832 670 A1  4/1998

* cited by examiner

*Primary Examiner*—Henry Bennett
*Assistant Examiner*—Nihir Patel
(74) *Attorney, Agent, or Firm*—Davis & Bujold, P.L.L.C.

(57) ABSTRACT

A balloon catheter is provided with a core insertable from a connector into an inside of a shaft. When an operation for insertion/retraction of the core is carried out by pinching an operating part, the core slides along the shaft and the depth of the core in the shaft is thereby adjusted. When the core is inserted deeper in the shaft, the region of the shaft with a high rigidity increases with the core out to the shaft's distal end. On the other hand, when the core is retracted to the fore side, the rigidity of the shaft at its distal end side becomes lower and the flexibility of the balloon catheter becomes higher.

6 Claims, 2 Drawing Sheets

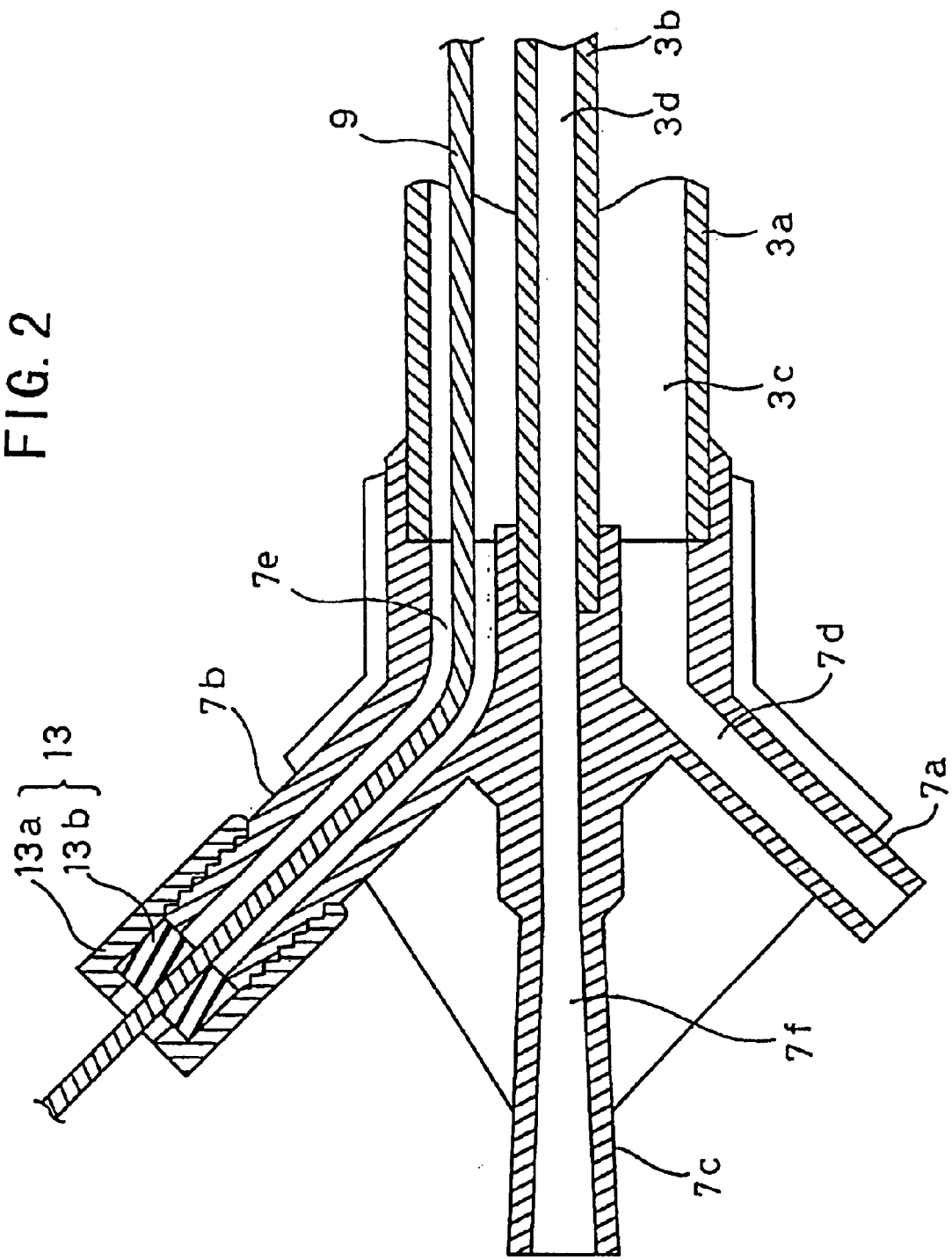

BALLOON CATHETER

FIELD OF INVENTION

This invention is related to balloon catheters.

BACKGROUND OF THE INVENTION

Heretofore, balloon catheters have been used, for example, for the percutaneous transluminal coronary angioplasty or PTCA. One such balloon catheter comprises of a thin flexible shaft and a balloon disposed on the distal end of the shaft. When fluid is supplied to or removed from the proximal end of the shaft via a supply/removal path for liquid, the balloon on the distal end of the shaft inflates or contracts.

In general, the shaft of the balloon catheter has high flexibility. High flexibility ensures that the shaft can flexibly curve along a bending blood vessel to smoothly guiding the balloon catheter into the vessel. But having a shaft with high flexibility naturally lacks rigidity and therefore provides poor pushability in the operation of the balloon catheter.

To improve on the above mention problem a balloon catheter having a core made of metal wire or the like fixed inside the shaft was provided. Since such a balloon catheter had a higher rigidity due to its core, the pushability in the operation of the balloon catheter was improved compared to a balloon catheter without a core. However, to some extent the flexibility of the shaft was sacrificed due to the more rigid core.

In the case of a conventional balloon catheter, though either one of flexibility or pushability was alternatively improved depending on whether the shaft of balloon catheter had a core or not, another important property is sacrificed. Once either type of a balloon catheter is chosen adjusting for flexibility or pushability during the operation of the balloon catheter that corresponds to encountered circumstances is impossible.

SUMMARY OF THE INVENTION

Wherefore, an object of the present invention is to provide a balloon catheter whose flexibility or pushability can be controlled depending on encountered circumstances during its operation.

In order to achieve the above and other objects, the present invention provides a balloon catheter having a thin and flexible shaft in which a fluid supply/removal path extends from the proximal end to the distal end. To the distal end of the shaft a balloon is secured. The balloon is inflated when fluid is supplied into its inside via the fluid supply/removal path, and is contracted when the fluid in its inside is removed. Finally, a core is provided in such a way that the core is inserted into the shaft from the proximal end of the shaft into its inside, and is slidable along the shaft. It is to be appreciated that allowing the tip end of the core to protrude from the shaft is prevented.

For the balloon catheter of the present invention, its structure and material are the same as those for a conventional balloon catheter. Typically, the balloon is made of a moldable polymer like, for example, polyurethane, latex, silicone rubber, natural rubber, polyvinyl chloride, polyamide, polyamide elastomer, copolymer of ethylene and vinyl acetate, polyethylene, polyimide, polyethylene terephthalate, fluorine resin and the like. However, it is to be appreciated that any other resin which is flexibly extendable and shrinkable, and is harmless as a medical apparatus can also be used, as there is no special limitation on such useable materials. Additionally, the shaft may be made of any material similar to that of the balloon so long as the material used can be flexibly bent while maintaining the form of the lumen.

To increase rigidity, the shaft has an insertable core. This core is made of a material which increases rigidity of the shaft without sacrificing for the lowest flexibility demanded of the shaft. Specifically, a metal wire thinner than the shaft or the like is used. Preferably, the metal wire has sufficient rigidity, even though very thin, and such tenacity that it does not break when bent. More specifically, such a metal used includes stainless steel, tungsten, nickel- titanium alloy, amorphous alloy and the like.

The core of the present invention is arranged in such a way that its end cannot protrude to the outside of the shaft. Various arrangement structures can be applied. For example, while a receiving space for a core is kept in the shaft, the length of the core insertable into the shaft is made shorter than the length of the receiving space. Such a structure prevents the core from protruding outside of the shaft. Since the end part of the core cannot protrude to the outside of the receiving space, the distal end of the receiving space may be of any structure. Alternatively, by applying a structure in which the end part of the core abuts the distal end of a wall defining the receiving space, the end part of the core is prevented from being protruded to the outside of the shaft. In this alternative embodiment the distal end of the wall defining the receiving space should be formed in such a way to prevent problems from occurring should the core abut the distal end of the wall. Further, in this alternative embodiment the core is not restricted concerning its total length and can be made, for example, excessively long, since the core cannot be further pushed into the receiving space, once the end part of the core abuts the distal end of the wall.

Though either a gas or liquid can be used as the fluid for inflating the balloon, liquid is more preferable because of the lesser effect pressure has on changing the volume of an inflated balloon. Such a liquid includes a physiological salt solution, a solution containing contrast medium or the like. In the case of gas, an inactive gas like helium is preferable.

When using the present invention, for example, when the stenosed part of the blood vessel is to be expanded with a catheter, the balloon catheter is inserted into the blood vessel in the same manner as a conventional balloon catheter. The difference being the slidable core of the catheter, which when slid towards the distal end, provides a higher rigidity to its influenced part of the shaft, while the uninfluenced part remains more flexible. Conversely, when the core is slid towards the proximal end, the part of the shaft without the core's influence becomes more flexible, while the part of the shaft with the core remains less flexible. Therefore, the flexibility and the pushability of the balloon catheter of the invention can be adjusted depending on the circumstances encountered when in use.

Specifically, in the circumstance where there is a bend in a blood vessel with the present invention an adjustment can be performed where the core is slid to the distal end side to keep good pushability until the catheter reaches the bent part of the blood vessel. Once at the bend, the core is then slid to the proximal end side in order to improve the flexibility of the distal end part of the shaft so that the catheter may pass through the bent part of the blood vessel. In this manner, the balloon catheter of the present invention makes its possible to adjust for flexibility or pushability during its operation to correspond to encountered circumstances.

The body conformation, the state of bending of the blood vessel and the distance from the insert portion of the catheter to the lesion of the patient differ depending on the patient to whom a balloon catheter is applied. By sliding the core corresponding to these conditions, the length of the shaft with high flexibility can be freely adjusted.

Moreover, as for the balloon catheter of the present invention, the core is preferably exchangeably formed by pulling out the core from the shaft. According to the balloon catheter formed in such a way, the rigidity of the shaft can be finely adjusted if only a few kinds of core are prepared, since the core can be pulled out from the shaft and exchanged. Needless to say, when fine adjustment of the rigidity of the shaft is unnecessary, the catheter may be formed in such a way that the core cannot be pulled out from the shaft or cannot be exchanged even if it can be pulled out (for example, a structure in which it is difficult for the core to be reinserted once it has been pulled out). Adopting a structure where the core cannot be pulled out from the shaft would avoid the trouble caused by a core being pulled by mistake.

The balloon catheter according to a further aspect of the invention has a structure in which the core or a part secured to the core can be secured to the shaft or to a part secured to the shaft.

Examples of a part secured to the core include a kind of knob secured to the core for easier insertion of the core, a stopper for preventing excessive insertion of the core by abutting the inlet of the shaft once the core is inserted by a predetermined length, and the like. The original usage of these parts is not especially limited. Needless to say, some other specific part may be used to secure the core to the shaft.

For a part secured to the shaft, examples include a securing piece for securing the shaft to the body of the patient or a connector fixed on the proximal end of the shaft. The original usage of these parts is not especially limited. Needless to say, some other specific part may be used to secure the shaft to the core.

According to the balloon catheter of the present invention, by securing the core or the part secured to the core (these will be called a "core side part" hereafter) to the shaft or the part secured to the shaft (these will be called a "shaft side part", hereafter), any relative displacement between the core and the shaft can be prevented from occurring. Therefore, effectively preventing the trouble associated with displacing the core relative to the shaft, thus effecting the portion of higher rigidity in part of the shaft, to an unexpected length during the insertion of the catheter.

As for the balloon catheter, any structure can be adopted even if the structure is formed in such a way that the securing of the core side part to the shaft side part is performed after the relative position of both parts has been determined. For example, a securing mechanism may be adopted in which the core side part and the shaft side part provided with a protrusion and a recess, respectively (or a recess and a protrusion, respectively) are engaged with each other, accompanied by elastic deformations. Alternatively, the core side part may be fixed to the shaft side part by means of a screw or the like, or the deviation between both parts may be prevented from occurring by the friction between the core side part and the shaft side part. Also, a structure can be adopted in which the relative position of the core side part and the shaft side part is continuously changed and they can be secured at any position. Furthermore, the structure may be such that both parts can be secured only when the relative position of the core side part and the shaft side part is changed to either of previously determined multiple positions.

The balloon catheter according to yet another aspect of the invention where the core is insertable into the fluid supply/removal path.

According to the balloon catheter with such a structure, the fluid supply/removal path used for supplying fluid to the balloon is also used as the space for housing the core. Therefore, the shaft can be thinner than a balloon catheter provided separately with a fluid supply/removal path and a housing space for a core. As a result, the catheter can be applied to thinner blood vessels, and to larger blood vessel in order to interrupt less of the blood flow when inserted.

The balloon catheter according to another aspect of the invention is provided with a connector which is disposed between the fluid supply source and the proximal end of the shaft connecting them together.

There are formed inside the connector a first passage connecting the fluid supply/removal path and the fluid supply source, and a second passage connecting the fluid supply/removal path and a core-inserting port into which the core can be inserted. Further, a closing part is provided inside the connector. The closing part can close the second passage to prevent fluid from flowing out from the second passage.

According to the balloon catheter formed in the above mentioned manner, the core is inserted through the core-inserting port and guided to the fluid supply/removal path via the second passage, while the fluid supplied from the fluid supply source flows into the fluid supply/removal path via the first passage. The first and second passages are both connected with the fluid supply/removal path. Therefore, the fluid flowing into the first passage also flows into the second passage, though the second passage can be closed with the closing part. Accordingly, the fluid is prevented from flowing out from the second passage, if the second passage is only closed with the closing part.

In the balloon catheter according to a further aspect of the invention, the closing part closes the second passage by abutting the outer periphery of the core with the core being inserted into the second passage, while the core is secured to the connector.

According to the balloon catheter formed in such a structure, there is no need to remove the core beforehand when the second passage is closed with the closing part. In addition, the whole structure can be made more compact, since no special parts are needed for securing the core side part to the shaft side part.

Though the structure of the catheter of the invention has been described before in detail, in addition to the aforementioned structure characteristic to the invention, any known structure adopted in such a kind of balloon catheter can be properly adopted.

Among such balloon catheters, for example, a catheter of so-called single lumen type provided only with a fluid supply/removal path, a catheter of so-called double lumen type provided with another path for inserting a guide wire in addition to the fluid supply/removal path, a catheter of multi-lumen type provided with other passages for discharging medicine or for maintaining the blood flow between both sides of the balloon and the like are used. The structure of a balloon catheter of the invention can be applied to any of these balloon catheters.

BRIEF DESCRIPTION OF THE DRAWINGS

FIG. 2 is a diagrammatic cross-sectional view showing the vicinity of the connector of aforementioned balloon catheter.

DETAILED DESCRIPTION OF THE PREFERRED EMBODIMENT OF THE INVENTION

Figure 1:
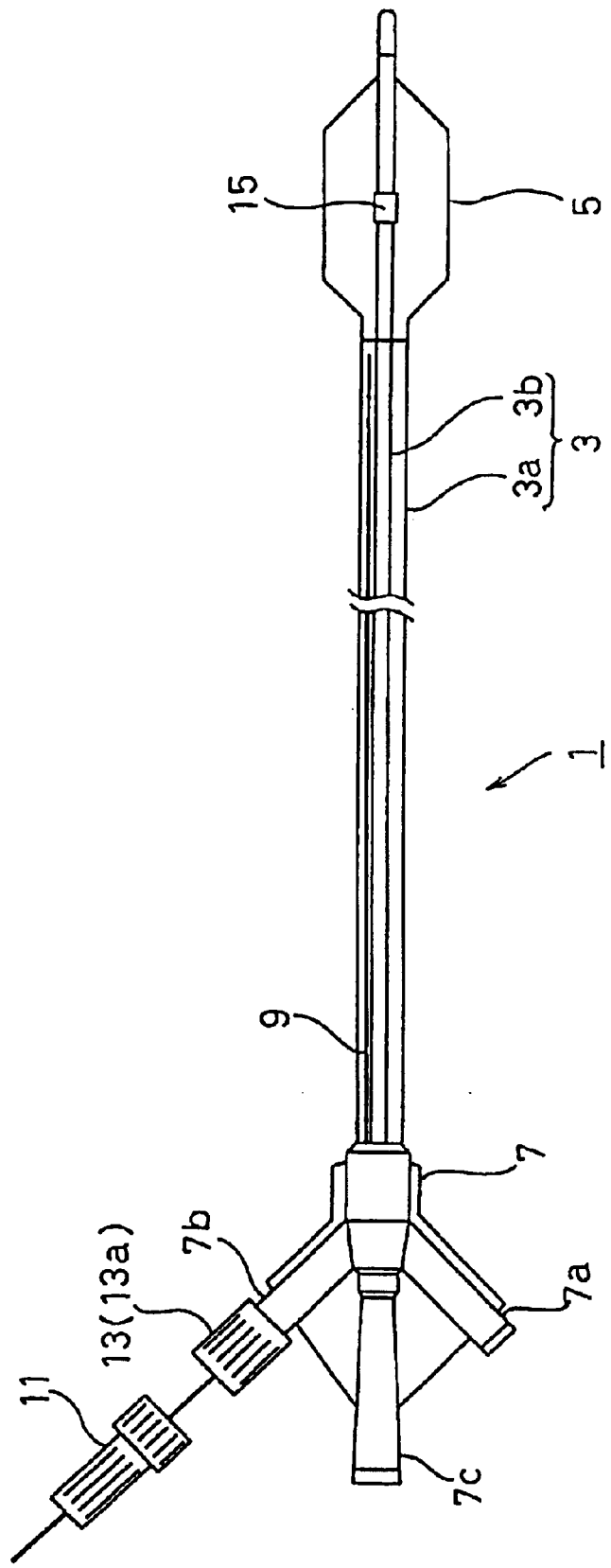
FIG. 1 is a side illustrative view showing the whole structure of the balloon catheter in the embodiment of the invention.

As shown in FIG. 1, a balloon catheter 1 is provided with a thin flexile shaft 3 made of polyethylene, a balloon 5 made of polyethylene secured to the distal end of the shaft 3, a connector 7 made of polycarbonate secured to the proximal end of the shaft 3 and a core 9 inserted into the shaft 3 from the side of the connector 7.

The shaft 3 is a double-walled tube. An inner tube 3b is inserted into an outer tube 3a of the shaft 3. A part of the inner tube 3b is protruded out from the distal end of the outer tube 3a, extending to the inside of the balloon 5. Though not shown in the figure, the outer tube 3a and the inner tube 3b is fixed to each other at several positions to prevent mutual displacement.

The balloon 5 is connected at its proximal end to the distal end of the outer tube 3a and at its distal end to the distal end of the inner tube 3b.

The connector 7 has a fluid supply port 7a protruding in the form of a tube, a core-inserting port 7b and a guide wire inserting-port 7c. As shown in FIG. 2, a first passage 7d extends from the fluid supply port 7a, a second passage 7e extends from the core inserting port 7b, and a third passage 7f extends from the guide wire inserting port 7c.

The inner face of the outer tube 3a and the outer face of the inner tube 3b form a space which is connected to the inside of the balloon 5. The space constitutes a fluid supply/removal path 3c. The lumen of the inside tube 3b also constitutes a guide wire inserting path 3d through which a guide wire is previously inserted into the blood vessel. The first passage 7d and the second passage 7e are both connected with the fluid supply/removal path 3c and the third passage 7f is connected with the guide wire inserting path 3d.

The core 9 is inserted from the core-inserting port 7b and guided to the fluid supply/removal path 3c in the shaft 3 via the second passage 7e in the connector 7. As shown in FIG. 1, an operation element 11 is fixed to the core 9. When an inserting/extracting operation is carried out by pinching the operation element 11, the core 9 is slid along the shaft 3 and the depth of insertion/retraction of the core 9 into the shaft 3 can be adjusted. The operation element 11 has such a size that it can not be inserted into the inside of the core-inserting port 7d. Additionally, the distance from the position where the operation element 11 is fixed to the distal end of the core 9 is designed such that the tip end of the core 9 cannot protrude to the outside of the shaft 3 even when the core 9 is inserted to its deepest position. Accordingly, since the core 9 cannot be over inserted into the shaft 3, the balloon 5 is prevented from being hurt by excessive insertion of the core 9.

Moreover, the core-inserting port 7b is provided with a closing part 13. As shown in FIG. 2, the closing part 13 is formed by an operation part 13a screwed to the core-inserting port 7b and a packing 13b spaced between the core-inserting port 7b and the operation part 13a. When the operation part 13a is rotated to the screwing direction, the packing 13b is elastically deformed by the pressure from the operation part 13a, thereby narrowing the inside diameter of the packing 13b. As a result, the packing 13b closely abuts the periphery of the core 9. In this condition, the fluid is prevented from flowing out from the inside of the port 7b. Moreover, since the packing 13b presses the surface of the core 9, the core 9 is prevented from being displaced. On the other hand, when the operation part 13a is rotated to a direction for loosening it, the packing 13b regains its original form, thereby widening its inside diameter. As a result, a space is formed between the packing 13b and the core 9. In this condition, the core 9 can be freely displaced.

In addition, as shown in FIG. 1, a marker 15 made of metal is secured on the periphery of the inner tube 3b in the balloon 5. When the catheter 1 is inserted into the body, it can be determined whether it gets to the expected position or not, by detecting the position of the marker 15 by means of X-ray.

The balloon catheter 1 constituted as aforementioned is used, for example, for expanding the stenosed part of the blood vessel with a balloon.

Specifically, after a guide wire is inserted into the blood vessel and passed through the stenosed part of the blood vessel beforehand, the balloon catheter 1 is inserted in the blood vessel using the guide wire, with the guide wire inserted into the guide wire inserting path 3d.

In this state, the core 9 is initially inserted into the deepest part of the shaft 3 providing rigidity to all of the shaft. Therefore, the shaft 3 has a high pushability and the inserting operation can be efficiently performed.

After some part of the balloon catheter 1 has been inserted into the body, flexibility occasionally becomes necessary for the balloon catheter 1, for example, when it can not be bent satisfactorily or tends easily to hurt the blood vessel if the shaft 3 keeps its high rigidity.

When such a circumstance is encountered, after loosening the closing part 13, the core 9 is pulled by a needed length toward the proximal end of the balloon catheter 1 and fixed at that position by screwing the closing part 13 again. By this operation, the distal end of the shaft 3 becomes less rigid allowing the shaft 3 to be flexibly bent. Therefore, the balloon catheter 1 can be pushed forward through the bend in the blood vessel without trouble. Since a necessary region of high rigidity can be kept by controlling the amount of the sliding of the core 9, decrease of the pushability of the shaft is limited to a minimum.

When the balloon 5 gets to the aimed position by pushing forward the balloon catheter 1, physiological salt solution (or any other liquid or gas) is supplied from the fluid supply port 7a to expand the balloon 5, thereby expanding the stenosed part of the blood vessel. In this time, the physiological salt solution also flows to the core-inserting port 7b. But the physiological salt solution does not leak out from the core-inserting port 7b, since the closing part 13 closes the second passage 7e. After necessary treatments, the physiological salt solution is removed from the fluid supply port 7a, the balloon 5 is contracted and the balloon catheter 1 is pulled out from the patient body.

As explained above, according to the aforementioned balloon catheter 1, the flexibility and pushability of the shaft 3 can be adjusted depending on the circumstances, even when the balloon catheter 1 is in use. Therefore, with the present invention minium time is wasted for the inserting operation since pushability is no longer aggravated due to too much flexibility, or is the catheter unable to be smoothly bent due to too much pushability.

Since the core 9 is inserted into the fluid supply/removal path 3c of the shaft 3, the shaft 3 can be made thinner compared with the case where an specific housing space for inserting the core 9 is formed in the shaft 3. Moreover, when a structure in which the core 9 is inserted into the fluid supply/removal path 3c is adopted, the fluid can also flow into the core-inserting path of the core 9. But the fluid is prevented from being leaked out from the core-inserting port 7b, since the aforementioned balloon catheter is provided with the closing part 13. In addition, since the closing part 13 prevents an unexpected displacement of the core 9 by closely abutting the core 9, the whole structure can be made more compact than a structure where the means for preventing such a displacement is separately provided in addition to the closing part 13.

Though a preferred embodiment of the invention was explained above, there are various modifications other than the aforementioned embodiment concerned to the invention.

Though in the aforementioned balloon catheter 1, the shaft 3 consists of the outer tube 3a and the inner tube 3b (so-called double lumen type), a similar balloon catheter can be constituted, when, for example, a shaft with two parallel lumens is adopted. In that case, the rigidity of the shaft can be adjusted by using a core like the aforementioned core. A balloon catheter of so-called single lumen type may also be constituted by using a shaft with one lumen. In the case, too, the rigidity of the shaft can be adjusted by using a core like the aforementioned core.

Despite the use of the specific embodiment for illustration purposes, the invention is intended to include all such modifications and alterations within the spirit and scope of the appended claims.

What is claimed is:

1. A balloon catheter comprising
    a thin and flexible shaft having a fluid supply and removal path extending from a proximal end of the shaft to a distal end of the shaft; and
    a balloon secured to the distal end of the shaft, the balloon being inflated when a fluid is supplied to an inside of the balloon, via the fluid supply and removal path, and the balloon being contracted when the fluid is removed from inside of the balloon, via the fluid supply and removal path;
    wherein a rigidity control core, more rigid than the shaft, is provided so that the rigidity control core is inserted from the proximal end of the shaft to a position adjacent the balloon and the rigidity control core is slidable substantially along an entire length of the shaft to select a rigidity of the shaft in a region of the rigidity control core, and a tip end of the rigidity control core is prevented from protruding out from the shaft.

2. The balloon catheter according to claim 1, wherein the balloon catheter has a structure in which the rigidity control core or a part secured to the rigidity core can be secured to the shaft or to a part secured to the shaft.

3. The balloon catheter according to claim 1, wherein the rigidity control core is inserted into and directly communicates with the fluid supply and removal path of the balloon catheter.

4. The balloon catheter according to claim 2, wherein the rigidity control core is inserted into and directly communicates with the fluid supply and removal path of the balloon catheter.

5. A balloon catheter comprising:
    a thin and flexible shaft having a fluid supply and removal path extending from a proximal end of the shaft to a distal end of the shaft; and
    a balloon secured to the distal end of the shaft, the balloon being inflated when a fluid is supplied to an inside of the balloon, via the fluid supply and removal path, and the balloon being contracted when the fluid is removed from inside of the balloon, via the fluid supply and removal path;
    wherein a rigidity control core, more rigid than the shaft, is provided so that the rigidity control core is inserted from the proximal end of the shaft to a position adjacent the balloon and the rigidity control core is slidable along the shaft to select a rigidity of the shaft in a region of the rigidity control core, and a tip end of the rigidity control core is prevented from protruding out from the shaft;
    a first passage and a second passage are formed in the proximal end of the shaft and both the first and second passages communicate with the fluid supply and removal path, a connector interconnects a fluid supply source with the first passage for supplying fluid from the fluid supply source to the fluid supply and removal path and the second passage connects the fluid supply and removal path with a core-inserting port into which the rigidity control core is insertable, and a closing part is provided for closing and sealing the second passage and preventing the fluid from flowing out through the second passage.

6. A balloon catheter comprising:
    a thin and flexible shaft having a fluid supply and removal path extending from a proximal end of the shaft to a distal end of the shaft; and
    a balloon secured to the distal end of the shaft, the balloon being inflated when a fluid is supplied to an inside of the balloon, via the fluid supply and removal path, and the balloon being contracted when the fluid is removed from inside of the balloon, via the fluid supply and removal path;
    wherein a rigidity control core, more rigid than the shaft, is provided so that the rigidity control core is inserted from the proximal end of the shaft to a position adjacent the balloon and the rigidity control core is slidable along the shaft to select a rigidity of the shaft in a region of the rigidity control core, and a tip end of the rigidity control core is prevented from protruding out from the shaft;
    a first passage and a second passage are formed in the proximal end of the shaft and both the first and second passages communicate with the fluid supply and removal path, a connector interconnects a fluid supply, source with the first passage for supplying fluid from the fluid supply source to the fluid supply and removal path and the second passage connects the fluid supply and removal path with a core-inserting port into which the rigidity control core is insertable, and a closing part is provided for closing and sealing the second passage and preventing the fluid from flowing out through the second passage; and
    the closing part closes the second passage by abutting and sealing against an outer periphery of the rigidity control core when the rigidity core is inserted into the second passage.

* * * * *